(12) United States Patent
Kato et al.

(10) Patent No.: US 11,883,141 B2
(45) Date of Patent: Jan. 30, 2024

(54) BIOLOGICAL INFORMATION MEASUREMENT APPARATUS AND BIOLOGICAL INFORMATION MEASUREMENT METHOD

(71) Applicants: OMRON HEALTHCARE Co., Ltd., Kyoto (JP); Osaka University, Osaka (JP)

(72) Inventors: Yuki Kato, Kyoto (JP); Shingo Yamashita, Kyoto (JP); Toshihiko Ogura, Kyoto (JP); Shunsuke Yoshimoto, Osaka (JP); Masataka Imura, Osaka (JP); Osamu Oshiro, Osaka (JP)

(73) Assignees: OMRON HEALTHCARE Co., Ltd., Kyoto (JP); OSAKA UNIVERSITY, Osaka (JP)

( * ) Notice: Subject to any disclaimer, the term of this patent is extended or adjusted under 35 U.S.C. 154(b) by 269 days.

(21) Appl. No.: 15/916,007

(22) Filed: Mar. 8, 2018

(65) Prior Publication Data

US 2018/0192896 A1  Jul. 12, 2018

Related U.S. Application Data

(63) Continuation of application No. PCT/JP2016/076775, filed on Sep. 12, 2016.

(30) Foreign Application Priority Data

Sep. 16, 2015  (JP) ................................. 2015-183269

(51) Int. Cl.
*A61B 5/022*  (2006.01)
*A61B 5/0225*  (2006.01)
(Continued)

(52) U.S. Cl.
CPC ............ *A61B 5/0225* (2013.01); *A61B 5/026* (2013.01); *A61B 5/0261* (2013.01);
(Continued)

(58) Field of Classification Search
None
See application file for complete search history.

(56) References Cited

U.S. PATENT DOCUMENTS 5,467,771 A * 11/1995 Narimatsu ............. A61B 5/021
600/485
5,497,779 A * 3/1996 Takaya .................. A61B 5/021
600/485
(Continued)

FOREIGN PATENT DOCUMENTS

CN  1518470 A  8/2004
CN  1631319 A  6/2005
(Continued)

OTHER PUBLICATIONS

International Search Report issued in Application No. PCT/JP2016/076775, dated Nov. 8, 2016 (4 pages).
(Continued)

*Primary Examiner* — Alex M Valvis
*Assistant Examiner* — Aurelie H Tu
(74) *Attorney, Agent, or Firm* — Osha Bergman Watanabe & Burton LLP

(57) ABSTRACT

A biological information measurement apparatus includes: a pressure sensor including a pressure detecting element; a pressing mechanism which presses the pressure sensor against an artery in a living body; a press controller which controls a pressing force of the pressing mechanism; a blood flow sensor; a blood flow information measurer which measures blood flow information based on output of the blood flow sensor; a pressing force decider which decides a
(Continued)

first pressing force based on blood flow information measured during a pressing force control time period when the pressing force is changed in one direction, and information of a pressure pulse wave detected during the pressing force control time period; and a record controller which records a pressure pulse wave detected in a first state where the pressing force is controlled to the first pressing force, and blood flow information measured in the first state.

7 Claims, 7 Drawing Sheets

(51) Int. Cl.

| | | |
|---|---|---|
| A61B 5/026 | (2006.01) | |
| A61B 5/00 | (2006.01) | |
| A61B 8/06 | (2006.01) | |
| A61B 5/021 | (2006.01) | |
| A61B 5/024 | (2006.01) | |

(52) U.S. Cl.
CPC ...... *A61B 5/02108* (2013.01); *A61B 5/02116* (2013.01); *A61B 5/02438* (2013.01); *A61B 5/6824* (2013.01); *A61B 5/6843* (2013.01); *A61B 8/06* (2013.01)

(56) References Cited

U.S. PATENT DOCUMENTS

| | | | | |
|---|---|---|---|---|
| 5,772,602 A * | 6/1998 | Sakai | ............... | A61B 5/022 |
| | | | | 600/495 |
| 5,791,348 A * | 8/1998 | Aung | ............... | A61B 5/02116 |
| | | | | 600/493 |
| 6,602,198 B2 * | 8/2003 | Yokozeki | ............... | A61B 5/021 |
| | | | | 600/500 |
| 6,602,200 B1 * | 8/2003 | Kubo | ............... | A61B 5/0225 |
| | | | | 600/485 |
| 7,976,471 B2 * | 7/2011 | Martin | ............... | A61B 5/7282 |
| | | | | 600/490 |
| 2001/0003792 A1 * | 6/2001 | Ogura | ............... | A61B 5/021 |
| | | | | 600/500 |
| 2002/0038090 A1 | 3/2002 | Sunagawa et al. | | |
| 2002/0107450 A1 * | 8/2002 | Ogura | ............... | A61B 5/0285 |
| | | | | 600/490 |
| 2002/0143260 A1 | 10/2002 | Ogura | | |
| 2004/0260184 A1 * | 12/2004 | Narimatsu | ............... | A61B 5/021 |
| | | | | 600/481 |
| 2010/0160794 A1 * | 6/2010 | Banet | ............... | A61B 5/0402 |
| | | | | 600/485 |
| 2010/0204588 A1 * | 8/2010 | Kim | ............... | A61B 5/021 |
| | | | | 600/485 |
| 2010/0331709 A1 * | 12/2010 | Matsumura | ............... | A61B 5/02422 |
| | | | | 600/490 |
| 2013/0211268 A1 | 8/2013 | Fujii et al. | | |

FOREIGN PATENT DOCUMENTS

| | | |
|---|---|---|
| CN | 103153176 A | 6/2013 |
| EP | 0330463 A1 | 8/1989 |
| JP | H01-214335 A | 8/1989 |
| JP | H02-019141 A | 1/1990 |
| JP | 2001-017399 A | 1/2001 |
| JP | 2002-051995 A | 2/2002 |
| JP | 2002-291709 A | 10/2002 |
| JP | 2006-115979 A | 5/2006 |
| JP | 2006-311951 A | 11/2006 |
| JP | 2008-183414 A | 8/2008 |
| JP | 2008183414 A * | 8/2008 |
| JP | 2013-085559 A | 5/2013 |
| WO | 02092169 A1 | 11/2002 |

OTHER PUBLICATIONS

Written Opinion issued in Application No. PCT/JP2016/076775, dated Nov. 8, 2016 (3 pages).
Office Action issued in Chinese Application No. 201680052406.1, dated May 26, 2020 (13 pages).

* cited by examiner

BIOLOGICAL INFORMATION MEASUREMENT APPARATUS AND BIOLOGICAL INFORMATION MEASUREMENT METHOD

CROSS-REFERENCE TO RELATED APPLICATION(S)

This application is a continuation of PCT application No. PCT/JP2016/076775, which was filed on Sep. 12, 2016 based on Japanese Patent Application (No. 2015-183269) filed on Sep. 16, 2015, the contents of which are incorporated herein by reference.

BACKGROUND

1. Technical Field

The present invention relates to a biological information measurement apparatus and a biological information measurement method.

2. Background Art

A biological information measurement apparatus is known that, in a state where a pressure sensor is in direct contact with a living body site through which an artery such as the radial artery in the wrist passes, measures biological information, for example, pulse information, blood pressure information, and the like by using information detected by the pressure sensor. Among such biological information measurement apparatuses, there is an apparatus on which a sensor for measuring the blood flow velocity is mounted.

Patent Literature 1 discloses a biological information measurement apparatus which non-invasively measures the blood flow velocity by using a pressure sensor for measuring a blood pressure, and which corrects the blood pressure that is measured based on a signal of the pressure sensor, by using the measured blood flow velocity.

Patent Literature 2 discloses a biological information measurement apparatus in which a pressure sensor for measuring the blood pressure, and a piezoelectric device for non-invasively measuring the blood flow velocity are closely placed, and which can measure blood pressure information and the blood flow velocity.

Patent Literatures 3 to 6 disclose biological information measurement apparatuses in which a pressure sensor for measuring the blood pressure and an ultrasonic device for non-invasively measuring the blood flow velocity are closely placed, and which can measure blood pressure information and blood flow information (the blood flow velocity and the blood flow volume).

Among the above, the apparatuses disclosed in Patent Literatures 4 to 6 decide an optimum pressing force which is to be applied when the pressure sensor for measuring the blood pressure is pressed against the living body, based on the output signal of the pressure sensor, and, in a state where an artery is pressed with the optimum pressing force, measure the blood flow velocity by using the ultrasonic device.

CITATION LIST

Patent Literature 1: JP-A-2006-311951
Patent Literature 2: JP-A-2008-183414
Patent Literature 3: JP-A-2006-115979
Patent Literature 4: JP-A-2001-017399
Patent Literature 5: JP-A-02-019141
Patent Literature 6: JP-A-01-214335

Patent Literatures 1 to 6 describe the tonometry method in which blood pressure information is calculated based on a pressure pulse wave that, in a state where an artery in the living body is compressed by a pressing surface in which a pressure detecting element is formed, is detected by the pressure detecting element.

In the tonometry method, a pressure pulse wave must be detected in a state where the blood vessel wall of an artery which is compressed by a pressing surface is flattened, and an influence of the tension of the blood vessel wall is reduced (hereinafter, sometimes referred to as the tonometry state).

In the case where a detection of a pressure pulse wave by the tonometry method, and a measurement of blood flow information are to be simultaneously performed in proximal sites, as described in Patent Literatures 1 to 6, blood flow information is detected in the tonometry state where the blood vessel wall is press flattened by a pressing surface. The state where the blood vessel wall is press flattened means a state where the blood vessel is partly constricted. Therefore, there is a possibility that blood flow information which is measured in this state may be deviated from the original value.

As a method of deciding an optimum pressing force that is a pressing force required for obtaining the tonometry state, there is a method in which, as described in Patent Literatures 4 to 6, a pressing force applied when the amplitude of a pressure pulse wave that is detected by a pressure sensor is maximum is decided as the optimum pressing force.

There is another method in which one of pressing forces during a period when the peak value of a pressure pulse wave that is detected by a pressure sensor is less varied is decided as the optimum pressing force.

When, as in these methods, the optimum pressing force is decided based on a pressure pulse wave that is detected by a pressure sensor, a case may occur where the conditions of measuring blood flow information are not optimum, and therefore there is a possibility that correct blood flow information cannot be measured. This problem is not appreciated in Patent Literatures 1 to 6.

SUMMARY

The invention has been conducted in view of the above circumstances. It is an object of the invention to provide a biological information measurement apparatus and biological information measurement method which can accurately detect a pressure pulse wave that is necessary for measuring biological information, while reducing an influence on the measurement accuracy of blood flow information.

According to an aspect of the invention, there is provided a biological information measurement apparatus of the invention including: a pressure sensor which includes a pressure detecting element; a pressing mechanism which is configured to press the pressure sensor against an artery in a living body; a press controller which is configured to control a pressing force to be exerted by the pressing mechanism; a blood flow sensor which is placed adjacent to the pressure sensor, and which is used for measuring blood flow information indicating a flow of blood that flows through the artery; a blood flow information measurer which is configured to measure blood flow information based on an output signal of the blood flow sensor; a pressing force decider which is configured to decide a first pressing force to be exerted by the pressing mechanism based on blood flow information that is measured by the blood flow information measurer during a pressing force control time period when the pressing force is changed in one direction by a control of the press controller, and information of a pressure pulse wave that is detected by the pressure detecting element during the pressing force control time period; and a record controller which, on a recording medium, is configured to record a pressure pulse wave that is detected by the pressure detecting element in a first state where the pressing force to be exerted by the pressing mechanism is controlled to the first pressing force by the pressing controller, and blood flow information that is measured by the blood flow information measurer in the first state.

According to an aspect of the invention, there is also provided a biological information measurement method of the invention including: a press controlling step of controlling a pressing force to be exerted by a pressing mechanism which is configured to press a pressure sensor against an artery in a living body, the pressure sensor including a pressure detecting element for detecting a pressure pulse wave; a blood flow information measuring step of measuring blood flow information based on an output signal of a blood flow sensor which is placed adjacent to the pressure sensor, and which is used for measuring blood flow information indicating a flow of blood that flows through the artery; a pressing force deciding step of deciding a first pressing force to be exerted by the pressing mechanism based on blood flow information measured in the blood flow information measuring step during a pressing force control time period when the pressing force is changed in one direction in the press controlling step, and information of a pressure pulse wave that is detected by the pressure detecting element during the pressing force control time period; and a record controlling step of, on a recording medium, recording a pressure pulse wave that is detected by the pressure detecting element in a first state where the pressing force to be exerted by the pressing mechanism is controlled to the first pressing force in the press controlling step, and blood flow information that is measured in the blood flow information measuring step in the first state.

DESCRIPTION OF EXEMPLARY EMBODIMENTS

Hereinafter, an embodiment of the invention will be described with reference to the drawings.

Figure 1:
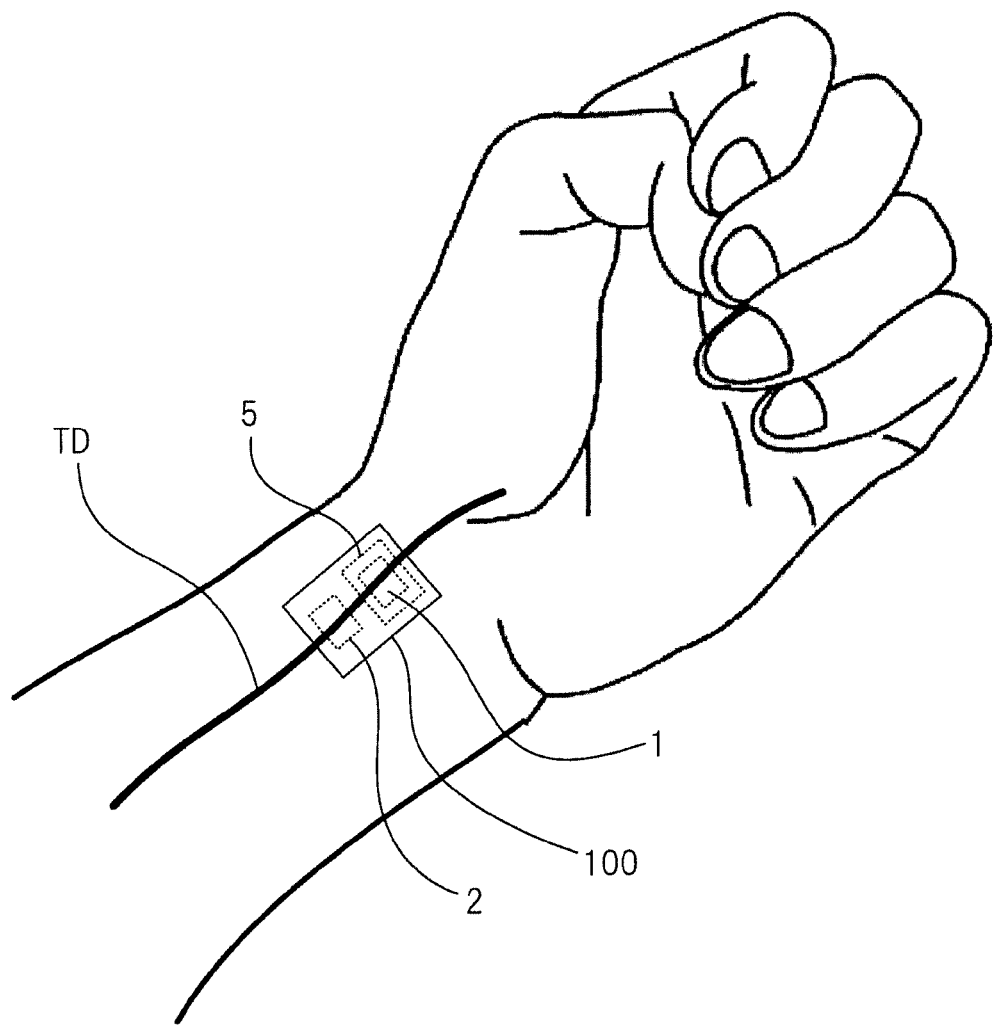
FIG. 1 is a diagram schematically showing the configuration of a biological information measurement apparatus 100 illustrating an embodiment of the invention.

FIG. 1 is a diagram schematically showing the configuration of a biological information measurement apparatus 100 illustrating an embodiment of the invention.

The biological information measurement apparatus 100 is used while attached by a belt that is not shown, to a living body site (in the example of FIG. 1, the wrist of the user) where an artery (in the example of FIG. 1, the radial artery TD) from which biological information is to be measured internally exists.

The artery from which biological information is to be measured is not limited to the radial artery TD, and another artery may be employed as the artery on which the measurement is to be performed.

The biological information measurement apparatus 100 includes as hardware a pressure sensor 1 which is used for detecting a pressure pulse wave from the radial artery TD, a pressing mechanism 5 which is used for pressing the pressure sensor 1 against the radial artery TD in the living body, and a blood flow sensor 2 which is placed adjacent to the pressure sensor 1, and which is used for measuring blood flow information indicating the flow of blood that flows through the radial artery TD.

In the example of FIG. 1, the blood flow sensor 2 is placed upstream of the pressure sensor 1 in the blood flow direction in the radial artery TD.

The blood flow sensor 2 is a sensor for non-invasively measuring the blood flow velocity as blood flow information. In the case where the blood flow velocity is measured by the ultrasonic Doppler method, an element which transmits an ultrasonic wave toward the artery, and that which receives the ultrasonic wave reflected from the artery are used in the blood flow sensor 2.

In the case where the blood flow velocity is measured by the laser Doppler method, alternatively, an element which illuminates the artery with a laser, and that which receives scattered light from the artery are used in the blood flow sensor 2.

The biological information measurement apparatus 100 simultaneously performs a process of recording a pressure pulse wave detected by the pressure sensor 1, and that of recording blood flow information which is measured based on an output signal of the blood flow sensor 2.

A meaning of the simultaneous measurements of a pressure pulse wave and the blood flow information is the knowing of, for example, the cause of variation of the blood pressure information and the pulse information from correlation of the blood pressure information (the systolic blood pressure, the diastolic blood pressure, and the pulse pressure) or pulse information which is produced based on the pressure pulse wave, and the blood flow information.

For example, other meanings are the estimation of the state of the peripheral side with respect to the measurement site, and that of the state of the central side with respect to the measurement site from correlation of the blood pressure information and the blood flow information.

In consideration of these meanings, preferably, the inter-sensor distance between the pressure sensor 1 and the blood flow sensor 2 is set to a small value such as from about 15 mm to 25 mm. However, the distance is not limited to this range.

Figure 2:
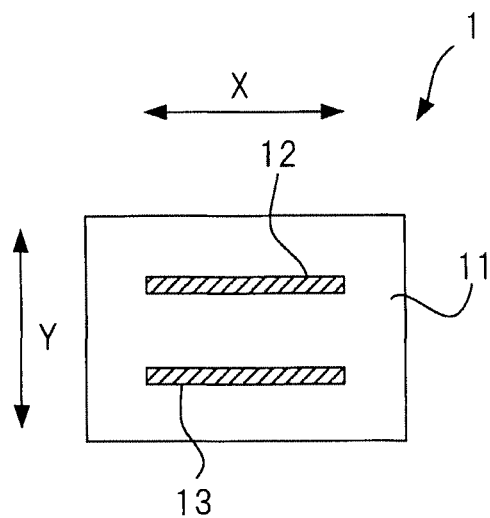
FIG. 2 is a planar diagram of a pressure sensor 1 of the biological information measurement apparatus 100 shown in FIG. 1, as viewed from the side of a contact surface with a living body.

FIG. 2 is a planar diagram of the pressure sensor 1 of the biological information measurement apparatus 100 shown in FIG. 1, as viewed from the side of a contact surface with the living body. As shown in FIG. 2, the pressure sensor 1 has an element row 12 and element row 13 which are formed on a planar substrate 11.

Each of the element row 12 and the element row 13 is configured by a plurality of pressure detecting elements which are arranged in a direction X perpendicular to the running direction of the radial artery TD from which a pressure pulse wave is to be measured.

Although the pressure detecting elements are not particularly limited, for example, elements in which the piezo resistance effect is used are employed. The element row 12 and the element row 13 are placed in juxtaposition with each other in a direction Y orthogonal to the direction X.

As described above, the pressure sensor 1 has the element row 12 and the element row 13. Therefore, the possibility that a pressure detecting element is placed directly above the radial artery TD which is in the tonometry state can be raised, and accurate detection of a pressure pulse wave is enabled.

Figure 3:
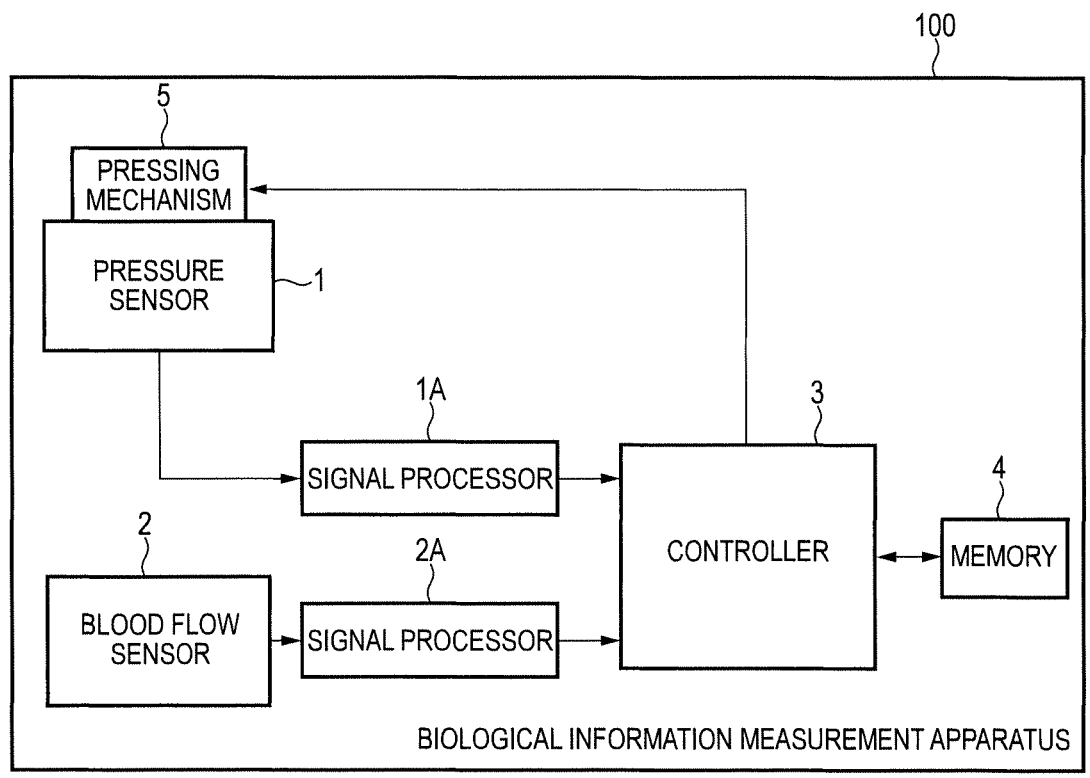
FIG. 3 is a block diagram showing the internal configuration of the biological information measurement apparatus 100 shown in FIG. 1.

FIG. 3 is a block diagram showing the internal configuration of the biological information measurement apparatus 100 shown in FIG. 1.

The biological information measurement apparatus 100 includes the pressure sensor 1, the blood flow sensor 2, a controller 3 which generally controls the whole configuration, a memory 4 including recording media such as a flash memory, a ROM (Read Only Memory), and a RAM (Random Access Memory), a signal processor 1A, a signal processor 2A, and the pressing mechanism 5.

In the biological information measurement apparatus 100, the configuration other than the pressure sensor 1, the blood flow sensor 2, the signal processor 1A, the signal processor 2A, and the pressing mechanism 5 may be placed in a place which is different from a case that is to be attached to a living body.

For example, the controller 3 and the memory 4 may be incorporated in a computer which is electrically connected to a case that accommodates the pressure sensor 1, the blood flow sensor 2, the signal processor 1A, the signal processor 2A, and the pressing mechanism 5.

The pressing mechanism 5 is a mechanism for pressing the pressure sensor 1 against the radial artery TD in the living body.

For example, the pressing mechanism 5 is configured by an air bag which is fixed to the substrate 11, and a pump for adjusting the internal pressure of the air bag. The pressing force (the internal pressure of the pump) which is exerted by the pressing mechanism 5 to be applied to the living body is controlled by the controller 3.

The signal processor 1A applies signal processing such as amplification processing and filtering processing to an output signal of the pressure sensor 1, and supplies the processed signal as the pressure pulse wave signal to the controller 3.

The signal processor 2A applies known signal processing which is known as the ultrasonic Doppler method, the laser Doppler method, or the like, to the output signal of the blood flow sensor 2 to produce information of the blood flow velocity, and supplies the information of the blood flow velocity to the controller 3.

The signal processor 2A functions as the blood flow information measurer which measures blood flow information based on the output signal of the blood flow sensor 2.

The controller 3 is configured mainly by a processor which executes programs stored in the memory 4, and, when the processor executes the programs, performs various kinds of processing.

Figure 4:
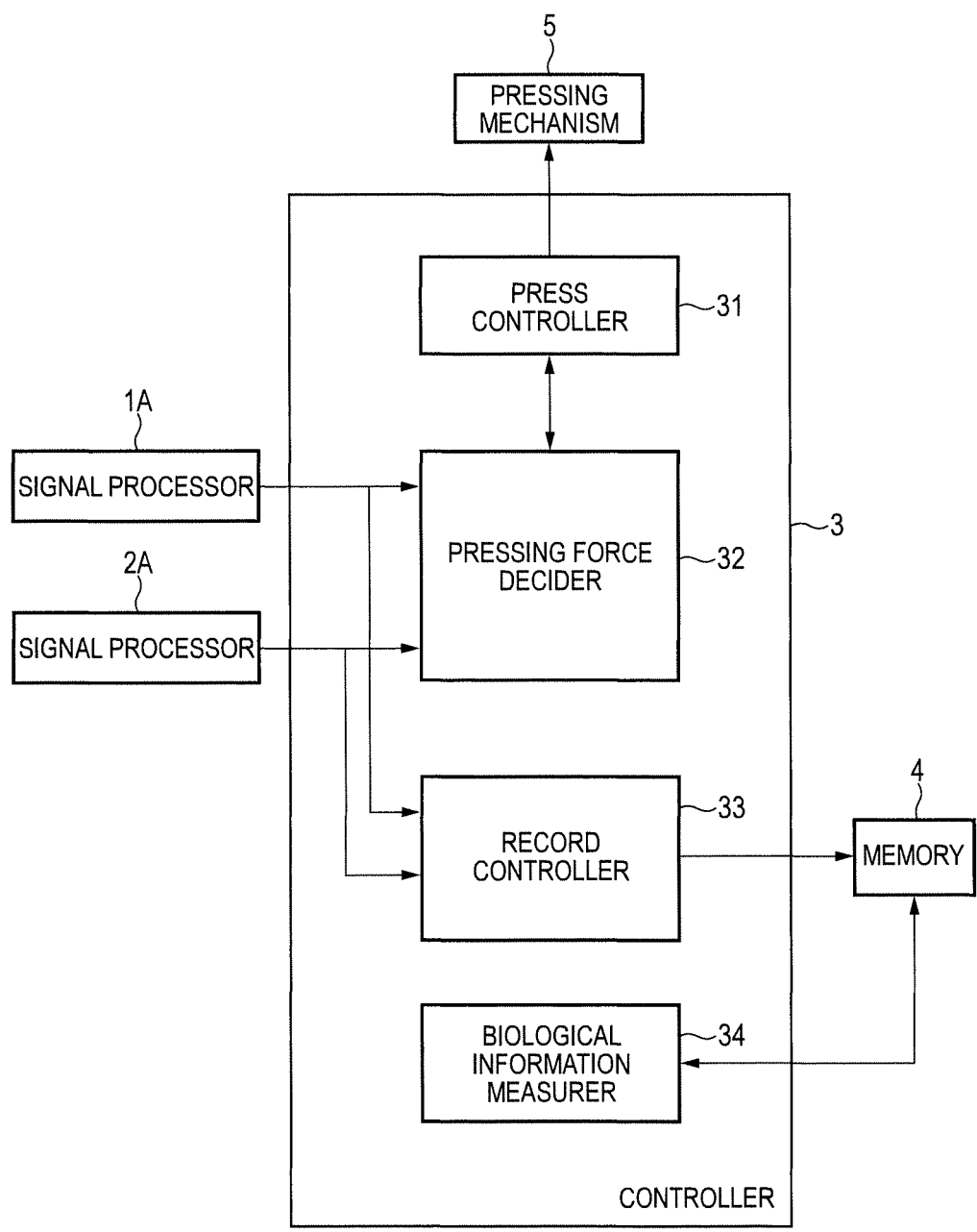
FIG. 4 is a functional block diagram of a controller 3 shown in FIG. 3.

FIG. 4 is a functional block diagram of the controller 3 shown in FIG. 3.

The controller 3 executes the programs to function as a press controller 31, a pressing force decider 32, a record controller 33, and a biological information measurer 34.

The press controller 31 drives the pressing mechanism 5 to control the pressing force which is exerted by the pressing mechanism 5, and which is then applied by the pressure sensor 1 to the radial artery TD.

At a predetermined timing such as that when the biological information measurement apparatus 100 is instructed to measure biological information, the press controller 31 performs a pressing force increasing control in which the pressing force exerted by the pressing mechanism 5 is increased from an initial value to a predetermined set value at a preset increase rate.

During a pressing force control time period which is a period when the pressing force increasing control is performed by the press controller 31, the pressing force decider 32 decides a first pressing force to be exerted by the pressing mechanism 5 based on information of the blood flow velocity measured by the signal processor 2A, and that of pressure pulse waves detected by the pressure sensor 1.

The pressure pulse wave which is detected by a pressure detecting element that is located directly above the portion where the radial artery TD is flat is not affected by the tension of the blood vessel wall of the radial artery TD, and has the largest amplitude. Moreover, the pressure pulse wave has the highest correlation with the blood pressure value in the radial artery TD.

Because of these reasons, the pressing force decider 32 sets the pressure detecting element which detects the pressure pulse wave having the maximum amplitude during the above-described pressing force control time period, as the optimum pressure detecting element, and decides the first pressing force to be exerted by the pressing mechanism 5 based on information of pressure pulse waves which are detected by the optimum pressure detecting element, and that of the blood flow velocity which is measured by the signal processor 2A during the pressing force control time period.

The first pressing force is a pressing force which realizes a state where a pressure pulse wave can be detected without being affected by a tension of the radial artery TD pressed with the first pressing force, in the circumferential direction of the blood vessel, i.e., the tonometry state, and that where the blood flow velocity is not changed (the error of measurement of the blood flow velocity is small) by deformation of the radial artery TD. A method of deciding the first pressing force will be described in detail later.

The record controller 33 performs a control in which the pressure pulse waves (the pressure pulse wave signal) that are detected by the optimum pressure detecting element of the pressure sensor 1 in a state where the pressing force exerted by the pressing mechanism 5 is controlled to the first pressing force by the press controller 31, and information of blood flow velocities that are measured by the signal processor 2A in this state are recorded in the memory 4 in association with time information.

The biological information measurer 34 measures biological information such as the systolic blood pressure, the diastolic blood pressure, the pulse pressure, and the pulse by a well-known method based on the pressure pulse wave signals which are detected by the optimum pressure detecting element in a state where the pressing force exerted by the pressing mechanism 5 is controlled to the above-described first pressing force by the press controller 31, and which are recorded in the memory 4. The measured biological information is recorded in the memory 4.

Next, the method of deciding the first pressing force will be described in detail.

Figure 5:
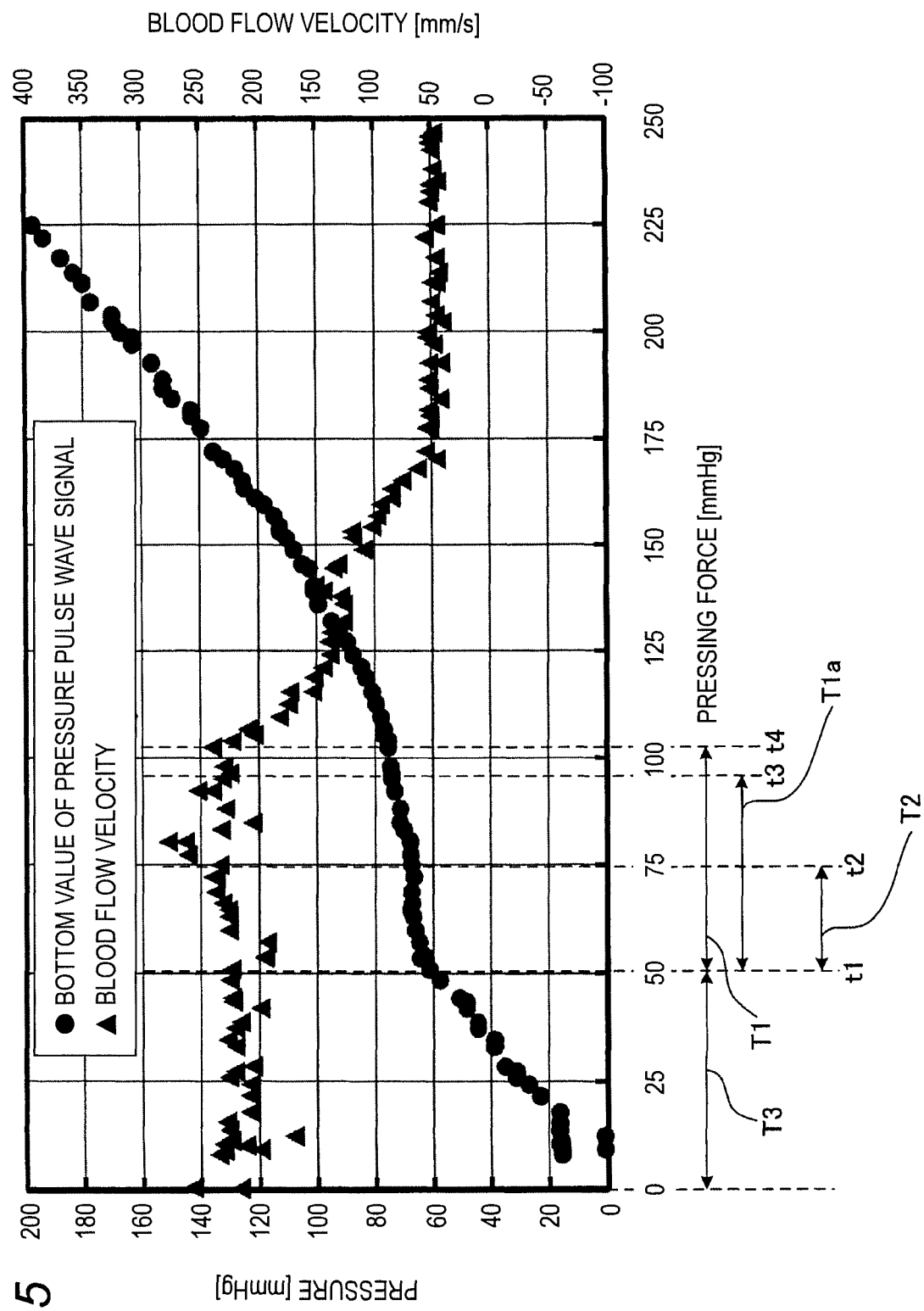
FIG. 5 is a view showing results of measurements in which a pressure pulse wave and the blood flow velocity were measured on the subject under measurement conditions similar to those in the biological information measurement apparatus 100.
Figure 6:
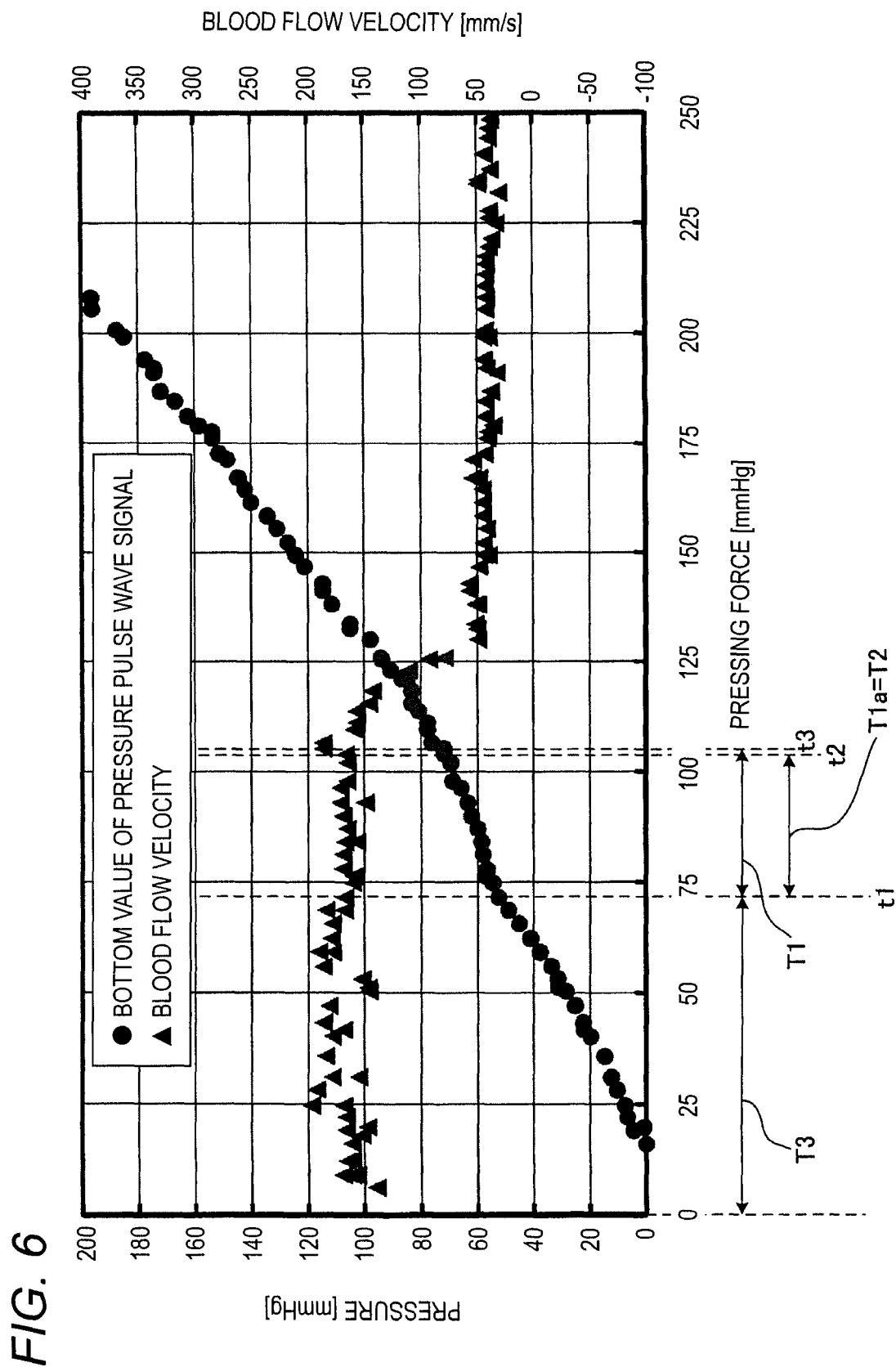
FIG. 6 is a view showing results of measurements in which a pressure pulse wave and the blood flow velocity were measured on a subject different from that of FIG. 5, under same measurement conditions similar to those in the biological information measurement apparatus 100.

FIGS. 5 and 6 are views showing results of measurements in which pressure pulse waves and blood flow velocities were measured on different subjects under measurement conditions similar to those in the biological information measurement apparatus 100.

FIGS. 5 and 6 are obtained by: setting the pressing force exerted by the pressing mechanism 5 as the abscissa; plotting the minimum value of the pressure pulse wave signals (the bottom value of the waveform of the pressure pulse wave) that were detected by the optimum pressure detecting element included in the pressure sensor 1 during the process of increasing the pressing force exerted by the pressing mechanism 5, as information of the pressure pulse waves on the ordinate; and similarly plotting the blood flow velocities that were measured by the signal processor 2A during the process, on the ordinate.

As shown in FIGS. 5 and 6, with respect to the information of pressure pulse waves, a feature is observed in which the information linearly increases when the pressing force starts to be increased, the increase rate becomes then once gentle, and thereafter the information linearly increases again.

It is considered that, during the period when the increase rate of the information of pressure pulse waves is gentle, an equilibrium state in which the intravascular pressure of the radial artery TD, and the pressing force pressing the radial artery TD are substantially equal to each other, i.e., the tonometry state exists.

In the example of FIG. 5, the time period T1 between the time t1 and the time t4 is a first time period when the increase rate of the information of pressure pulse waves is equal to or smaller than a threshold. In the example of FIG. 6, the time period T1 between the time t1 and the time t3 is a first time period when the increase rate of the information of pressure pulse waves is equal to or smaller than the threshold.

When only the accuracy of detection of a pressure pulse wave is considered, it is sufficient to decide either one of the pressing forces in the first time period as the above-described first pressing force.

Conventionally, it is usual that, during the time periods T1 shown in FIGS. 5 and 6, the pressing force at the timing when the change rate of the information of pressure pulse waves is minimum, or that when the pressure pulse wave having the maximum amplitude is detected is set as the first pressing force.

In the results of FIG. 5, however, there are timings when the blood flow velocity is sharply changed (for example, timings in the vicinity of a pressing force of 76 mmHg), during the time periods T1. When the first pressing force is decided in a conventional method, therefore, there is a possibility that, although the pressure pulse wave is accurately detected, a value which is largely deviated from the original one is measured with respect to the blood flow velocity.

The amount of blood supplied to the radial artery TD is varied by variation of the cardiac output due to respiration. Therefore, the blood flow velocity is somewhat dispersed even in, for example, a normal state where the blood vessel is not pressed. In FIG. 5, blood flow velocities which are detected at timings in the vicinity of a pressing force of 76 mmHg exceed the dispersion range.

Therefore, the pressing force decider 32 determines a second time period which is in a partial time period of the first time period when the change rate of the information of pressure pulse waves (the minimum value of the pressure pulse wave signal) detected during the pressing force control time period is equal to or smaller that a threshold, and which is a continuous time period when the blood flow velocity is within a predetermined range while setting the timing when the pressing force is controlled to be minimum, as the starting point. The pressing force decider decides one of pressing forces in the second time period, as the first pressing force.

Specifically, the pressing force decider 32 calculates the difference of information of pressure pulse waves detected at adjacent times in information of pressure pulse waves detected during the pressing force control time period, as the change rate of information of pressure pulse waves, and sets the time period when the difference is equal to or smaller than a threshold, as the first time period (in the examples of FIGS. 5 and 6, the time period T1) when the change rate of information of pressure pulse waves is equal to or smaller than the threshold.

Moreover, the pressing force decider 32 selects a time period (in the examples of FIGS. 5 and 6, the time period T1a) which is in the first time period, and which extends from the time (in the examples of FIGS. 5 and 6, the time t1) when the pressing force is controlled to be minimum, to the time (in the example of FIG. 5, the time t3, and, in the example of FIG. 6, the time t2) when the pressure pulse wave having the maximum amplitude is detected, as the partial time period of the first time period.

Furthermore, the pressing force decider 32 calculates the dispersion range of the blood flow velocity of the subject from following Expression (1) based on blood flow velocities measured in a third time period (in the examples of FIGS. 5 and 6, the time period T3) which is in the pressing force control time period, and during which the pressing force is controlled to be smaller than that in the first time period, and sets the range as the above-described predetermined range.

$$m_v - 3\sigma_v \leq v \leq m_v + 3\sigma_v \quad (1)$$

In Expression (1), "v" is the blood flow velocity. Moreover, "$m_v$" indicates the average value of blood flow velocities in the third time period, and is expressed by following Expression (2). In Expression (2), "n" indicates the number of blood flow velocities measured in the third time period. In Expression (2), "$v_i$" indicates the blood flow velocity measured in the i-th measurement in the third time period.

$$m_v = \frac{1}{n}\sum_{i=1}^{n} v_i \quad (2)$$

In Expression (1), "$\sigma_v$" indicates the standard deviation of blood flow velocities in the third time period, and is expressed by following Expression (3).

$$\sigma_v = \sqrt{\frac{1}{n}\sum_{i=1}^{n}(v_i - m_v)^2} \qquad (3)$$

The pressing force decider 32 determines the second time period which is a continuous time period when the blood flow velocity is within the predetermined range that is calculated by Expression (1) while setting the timing (the time t1 in FIGS. 5 and 6) when the pressing force is controlled to be minimum in the partial time period (the time period T1a in FIGS. 5 and 6) of the first time period, as the starting point.

In the example of FIG. 5, "$m_v$" is 220 mm/s, and "$3\sigma_v$" is 30 mm/s Therefore, the time period T2 which begins at the time t1, and which extends to the time t2 that is immediately before the time when the blood flow velocity exceeds for the first time a range of 220±30 mm/s is the second time period.

In the example of FIG. 6, "my" is 170 mm/s, and "$3\sigma_v$" is 45 mm/s. In the example of FIG. 6, the blood flow velocity does not exceed a range of 170±45 mm/s in the time period T1a, and therefore the time period T1a as it is becomes the second time period.

The second time period which is decided in this way is a time period when the tonometry state in which the intravascular pressure and the pressing force are substantially equal to each other is attained, and blood flow velocities are within the dispersion range. When one of pressing forces of the second time period is decided as the first pressing force, while accurately detecting the pressure pulse wave, therefore, the blood flow velocity can be accurately measured at the same time.

Several methods can be employed in deciding a pressing force in the second time period as the first pressing force.

(First Method)

The pressing force decider 32 decides the maximum one of pressing forces in the second time period (the time period T2 in FIG. 5, and the time period T1a in FIG. 6) as the first pressing force.

According to the first method, in the case of a subject in whom the blood flow velocity is not largely changed in the second time period, as the subject from whom the results of FIG. 6 were obtained, the pressing force in which the amplitude of the pressure pulse wave is maximum is decided as the first pressing force. Therefore, the pressure pulse wave can be highly accurately detected similarly with the prior art.

The early stage of the second time period can be said to be a state where the blood vessel wall of the radial artery TD begins to become flat. When a state where the pressing force is as large as possible is set as conditions for measurement of the pressure pulse wave as in the first method, therefore, the pressure pulse wave can be measured more accurately.

According to the first method, moreover, the process of deciding the first pressing force can be simplified, and the calculation process in the controller 3 can be reduced, whereby the processing load can be lowered. In the case where the biological information measurement apparatus 100 is driven by a battery, as a result, the continuous operating time can be prolonged.

(Second Method)

The pressing force decider 32 decides the pressing force at the timing when the pressure pulse wave having the maximum amplitude is detected, among pressing forces in the second time period (the time period T2 in FIG. 5, and the time period T1a in FIG. 6), as the first pressing force. The pressure pulse wave can be highly accurately detected also by the second method.

(Third Method)

The pressing force decider 32 decides the pressing force at the timing when the change rate of pressure pulse wave information is minimum, among pressing forces in the second time period (the time period T2 in FIG. 5, and the time period T1a in FIG. 6), as the first pressing force. The pressure pulse wave can be highly accurately detected also by the third method.

The pressing force decider 32 may determine the second time period while targeting the whole first time period. Namely, the pressing force decider 32 decides the continuous time period in which the timing (the time t1 in FIGS. 5 and 6) when the pressing force is controlled to be minimum in the first time period (the time period T1 of FIGS. 5 and 6) is set as the starting point, and the blood flow velocity is within the predetermined range calculated by Expression (1), as the second time period.

In the case of the pressing force in the first time period, the accuracy of detection of the pressure pulse wave can be sufficiently enhanced. Even in the configuration, therefore, the pressure pulse wave and the blood flow velocity can be detected simultaneously and accurately.

The operation of the thus configured biological information measurement apparatus 100 will be described.

Figure 7:
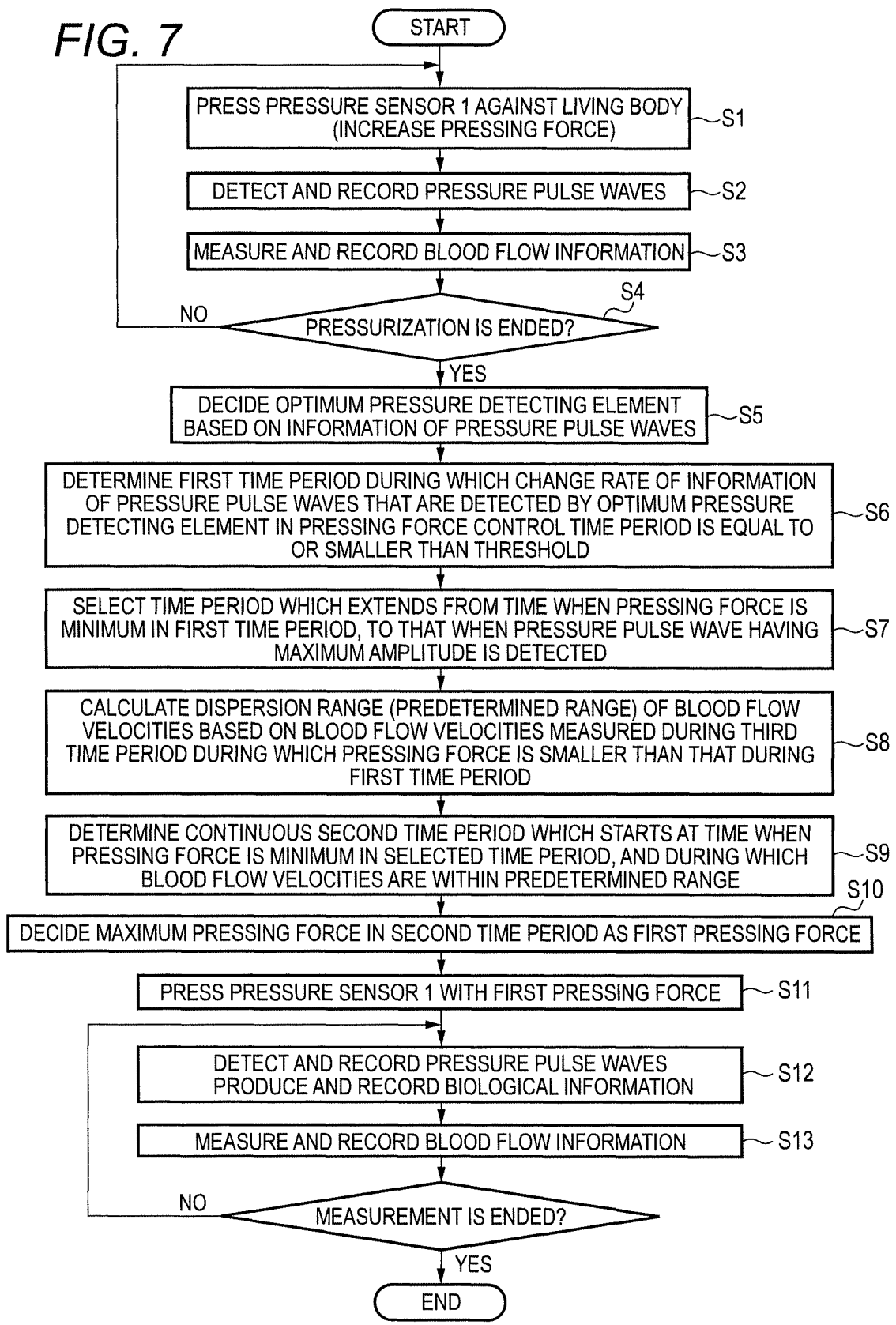
FIG. 7 is a flowchart illustrating the operation of the biological information measurement apparatus 100 shown in FIG. 1.

FIG. 7 is a flowchart illustrating the operation of the biological information measurement apparatus 100 shown in FIG. 1.

When the biological information measurement apparatus 100 is attached to the wrist of the user, a power supply is turned on by the user, and an operation of starting the measurement is done, the press controller 31 performs the pressing force increasing control in which the pressing force exerted by the pressing mechanism 5 is increased from an initial value by a predetermined amount (Step S1).

When the increase of the pressing force is started, pressure pulse waves are detected by the pressure sensor 1, and the pressure pulse wave signal is supplied to the pressing force decider 32. The pressing force decider 32 records the supplied pressure pulse wave signal in the memory 4 in correspondence with the detection time and the pressing force at the time (Step S2).

In parallel with the detection of pressure pulse waves, the blood flow velocity is measured by the blood flow sensor 2 and the signal processor 2A, and information of the blood flow velocity is supplied to the pressing force decider 32. The pressing force decider 32 records the supplied information of the blood flow velocity in the memory 4 in correspondence with the measurement time and the pressing force at the time (Step S3).

Next, the press controller 31 determines whether the pressing force is raised to a predetermined set value or not (Step S4). If the pressing force does not reach the set value (Step S4: NO), the press controller 31 causes the process to return to Step 1, and continues the increase of the pressing force. If the pressing force reaches the set value (Step S4: YES), the processes of Step S5 and subsequent steps are performed.

In Step S5, the pressing force decider 32 reads pressure pulse wave signals which are recorded in the memory 4, and which are detected during the pressing force increasing time period (the pressing force control time period), and decides the pressure detecting element which detects the pressure pulse wave signal having the maximum amplitude, as the optimum pressure detecting element.

Next, the pressing force decider 32 determines the first time period (in the example of FIG. 5, the time period T1) during which the change rate of the information (the minimum value of the pressure pulse wave signal) of pressure pulse waves that are detected in the pressing force control time period by the optimum pressure detecting element decided in Step S5 is equal to or smaller than the threshold (Step S6).

Next, the pressing force decider 32 selects the time period (in the example of FIG. 5, the time period T1a) which extends from the timing when the pressing force is minimum in the first time period determines in Step S6, to that when the pressure pulse wave having the maximum amplitude is detected (Step S7).

Next, the pressing force decider 32 calculates a predetermined range that is the dispersion range of the blood flow velocity of the user, from calculation of Expression (1) based on the blood flow velocity measured by the blood flow sensor 2 and the signal processor 2A in the third time period during which the pressing force is controlled to be smaller than that during the first time period in the pressing force control time period (Step S8).

Next, the pressing force decider 32 determines the continuous second time period (in the example of FIG. 5, the time period T2) which starts at the timing when the pressing force is minimum in the time period selected in Step S7, and during which blood flow velocities measured in this time period are within the predetermined range calculated in Step S8 (Step S9).

Next, the pressing force decider 32 determines the maximum pressing force in the second time period decided in Step S9, as the first pressing force (Step S10).

When the first pressing force is decided in Step S10, the press controller 31 drives the pressing mechanism 5 to control the pressing force to be exerted by the pressing mechanism 5 to the first pressing force (Step S11).

In the state where the pressing force is fixed to the first pressing force, then, pressure pulse waves are detected by the pressure sensor 1, and the pressure pulse wave signal is supplied to the pressing force decider 32. The pressing force decider 32 records the supplied pressure pulse wave signal in the memory 4 in correspondence with the detection time. Based on the pressure pulse wave signal, moreover, the biological information measurer 34 produces blood pressure information and pulse information, and records them in the memory 4 in correspondence with the detection time of the pressure pulse wave signal (Step S12).

In parallel with the detection of pressure pulse waves, the blood flow velocity is measured by the blood flow sensor 2 and the signal processor 2A, and information of the blood flow velocity is supplied to the pressing force decider 32. The pressing force decider 32 records the supplied information of the blood flow velocity in the memory 4 in correspondence with the measurement time (Step S13).

After Step S13, the controller 3 determines whether instructions for ending the measurements of the pressure pulse wave and the blood flow velocity are issued or not. If the instructions are not issued (Step S14: NO), the process is returned to Step S12, and, if the instructions are issued (Step S14: YES), the measuring process is ended.

As described above, the biological information measurement apparatus 100 decides the first pressing force to be exerted by the pressing mechanism 5, based on information of the blood flow velocity and pressure pulse wave which are measured during the pressing force control time period. In the state where the pressure sensor 1 is pressed against the living body with the first pressing force, then, the biological information measurement apparatus 100 detects and records pressure pulse waves, measures and records biological information based on the pressure pulse waves, and measures and records the blood flow velocity.

The first pressing force that is decided as described above is a pressing force which realizes the tonometry state, and which realizes a state where the blood flow velocity is not largely changed by deformation of the radial artery TD. In the state where the pressure sensor 1 is pressed against the living body with the first pressing force, when the detection of pressure pulse waves and the measurement of the blood flow velocity are simultaneously performed, therefore, pressure pulse waves that are necessary for measuring biological information can be accurately detected while reducing an influence on the measurement accuracy of the blood flow velocity. Consequently, the measurement of the blood flow velocity, and that of the pressure pulse wave can be performed simultaneously and accurately, and they can be used in diagnosis of various diseases.

Moreover, the biological information measurement apparatus 100 obtains the dispersion range of the blood flow velocity of the subject from Expression (1) based on the blood flow velocity measured during, in the example of FIG. 5, the time period T3.

There is a possibility that the dispersion range of the blood flow velocity may be changed depending on the state of attachment of the biological information measurement apparatus 100 to the wrist, the condition of the subject, individual differences, and the like. According to the biological information measurement apparatus 100, the dispersion range of the blood flow velocity is calculated based on blood flow velocities which are measured from the subject during the pressing force control time period for deciding the first pressing force. Therefore, such a change of the dispersion range can be absorbed, and the first pressing force can be accurately decided.

The controller 3 of the biological information measurement apparatus 100 may record the predetermined range in the memory 4 after the predetermined range is calculated in Step S8 of FIG. 7, and, at start of measurement of the next and subsequent times after the measuring process of FIG. 7 is ended, read information of the predetermined range recorded in the memory 4 to decide the second time period. According to the configuration, the next and subsequent measuring processes can be simplified.

The biological information measurement apparatus 100 has the configuration in which the blood flow sensor 2 is placed on the upstream side of the radial artery TD in the blood flow direction, and the pressure sensor 1 is placed on the downstream side. Therefore, the accuracy of decision of the first pressing force can be improved. The reason will be described as follows.

Figure 8:
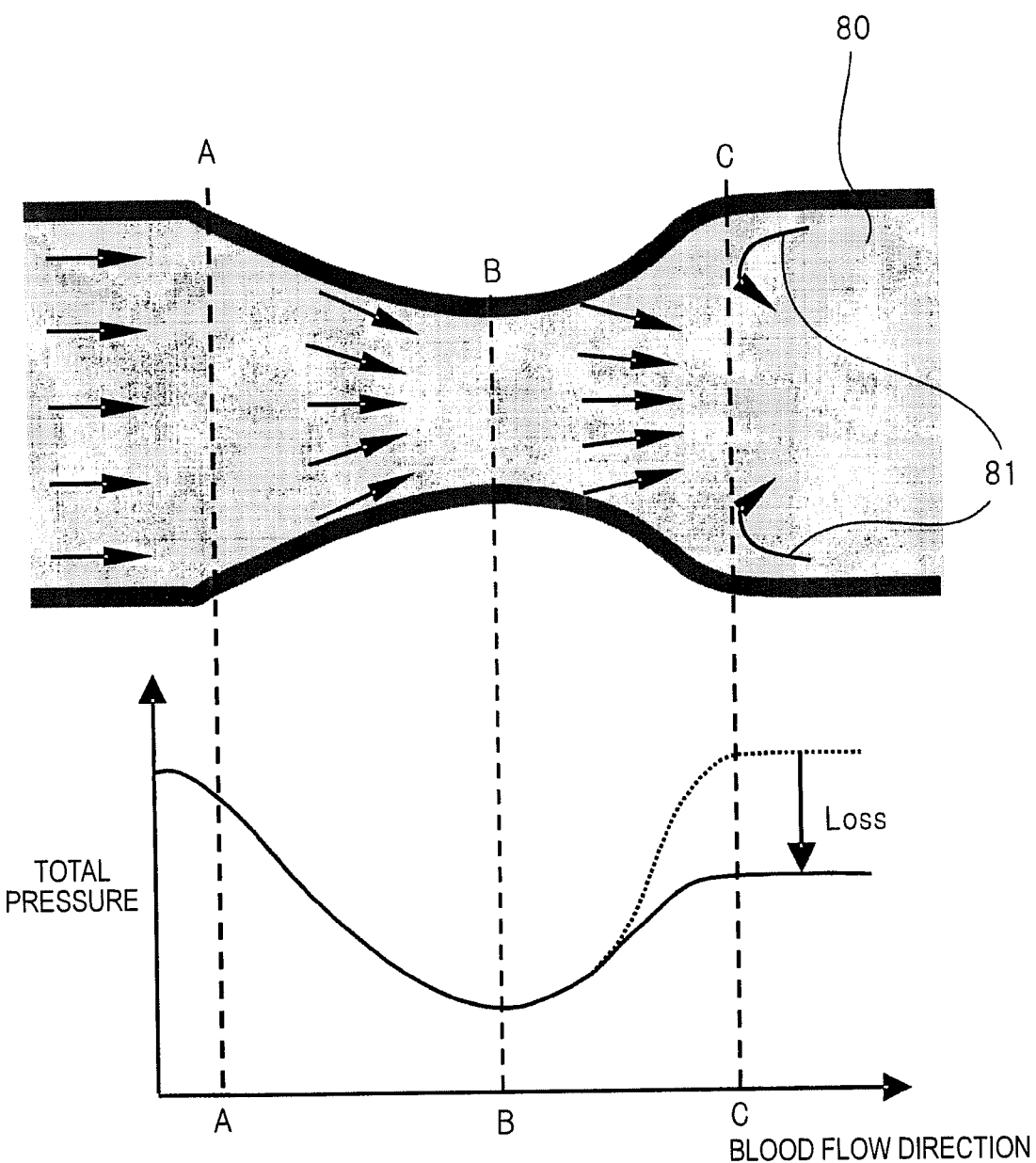
FIG. 8 is a view showing relationships of, in a state where a blood vessel is constricted, the total pressure of the whole blood vessel and a position in the blood flow direction.

FIG. 8 is a view showing relationships of, in a state where a blood vessel is constricted, the total pressure of the whole blood vessel and a position in the blood flow direction.

A blood vessel 80 shown in FIG. 8 is a model which is constricted in the range of the positions A to C, and which is thinnest at the position B. A graph showing the relationships of the position in the blood flow direction of the blood vessel 80 and the total pressure of the blood vessel 80 is shown below the blood vessel 80. In FIG. 8, the blood flows in the direction from the left to the right.

As shown in the graph, in the range of the positions A to B, the total pressure is reduced in the blood flow direction because of the vasoconstriction. In the range of the positions A to B, therefore, the blood flow velocity is increased as compared to the upstream side of the position A.

In the range of the positions B to C, by contrast, the blood vessel becomes gradually thicker, and therefore the total pressure is increased in the blood flow direction. In the range of the positions B to C, therefore, the blood flow velocity is reduced as compared to the range of the positions A to B.

In the vicinity of the position C, however, the blood flows from the narrow blood vessel portion to the wide blood vessel portion, and therefore the blood flow direction is not uniform in the direction from the upstream side to the downstream side, and forms a swirling shape. As shown in the graph, therefore, a pressure loss is generated in the vicinity of the position C by which the total pressure is lowered as compared to that in the upstream side of the position A.

Since a pressure loss is generated in the vicinity of the position C, there is a possibility that the blood flow velocity is increased as a whole. This phenomenon is seemed to be one of causes of the large change of the blood flow velocity which has been described in the example of FIG. 5, and which occurs in the time period T1 in the tonometry state.

The first pressing force which is decided by the pressing force decider 32 can be said to be a pressing force which is in the tonometry state, and the intensity of which is not sufficient for generating the pressure loss.

In consideration of the above-described principle of the pressure loss, when the blood flow sensor 2 is placed upstream of the pressure sensor 1 in the blood flow direction, the blood flow can be measured at a position where the blood flow velocity (or the blood flow direction) is relatively stabilized, by the blood flow sensor 2 and the signal processor 2A.

Therefore, the dispersion range of the blood flow velocity can be accurately calculated. As a result, the first pressing force can be accurately decided, and the accuracy of measurement of the blood flow velocity, and that of detection of the pressure pulse wave can be improved.

Of course, the biological information measurement apparatus 100 may have a configuration in which the blood flow sensor 2 is placed downstream of the pressure sensor 1 in the blood flow direction.

In the above description, it is assumed that, in Step S1 of FIG. 7, detection of the pressure pulse wave and measurement of the blood flow velocity are performed during the process in which the press controller 31 increases the pressing force, and the first pressing force is decided based on information of the pressure pulse wave and blood flow velocity which are obtained during the process.

The biological information measurement apparatus 100 may perform a control in which the pressing force is increased to the above-described set value, and thereafter reduced in steps of a predetermined amount, perform detection of the pressure pulse wave and measurement of the blood flow velocity during the process of reducing the pressing force, and decide the first pressing force based on information of the pressure pulse wave and blood flow velocity which are obtained during the process.

According to the above-described configuration in which the first pressing force is decided based on information of the pressure pulse wave and blood flow velocity which are obtained during the process of increasing the pressing force, variation of the blood flow velocity during the pressing force control time period can be prevented from being increased. Therefore, the first pressing force can be accurately decided.

In the biological information measurement apparatus 100, the bottom value of the pressure pulse wave signal is used as information of the pressure pulse wave which is used in Step S6 and subsequent steps of FIG. 7. In place of the value, the amplitude value of the pressure pulse wave signal or the peak value of the pressure pulse wave signal may be used. Even when any one of the values is used, substantially same results are obtained with respect to the first time period, and therefore similar effects as before can be attained.

Although the signal processor 2A of the biological information measurement apparatus 100 is assumed to measure the blood flow velocity as the blood flow information, the signal processor 2A may measure the blood flow volume.

In this case, a sensor for measuring the sectional area of the artery is placed in adjacent to the blood flow sensor 2. The signal processor 2A calculates the blood flow volume by multiplying the blood flow velocity which is calculated based on the output signal of the blood flow sensor 2, with the sectional area which is calculated based on output information of the sensor.

It is considered that the artery portion where the blood flow sensor 2 is to be placed has a substantially constant sectional area, and therefore the blood flow volume which is calculated as described above has a value which is proportional to the blood flow velocity. Therefore, the first pressing force can be decided also by using information of the blood flow volume in place of the blood flow velocity.

Alternatively, the blood flow volume can be obtained also by using the photoelectric volume pulse waveform. In the alternative, the biological information measurement apparatus 100 may have a configuration where a photoelectric pulse wave sensor is used in place of the blood flow sensor 2, and the signal processor 2A calculates the blood flow volume by using the photoelectric volume pulse waveform.

The pressure sensor 1 of the biological information measurement apparatus 100 has the configuration which has the plurality of element rows each configured by a plurality of pressure detecting elements. However, the pressure sensor 1 is required only to have a configuration which can detect a pressure pulse wave, and may have at least one pressure detecting element.

In the pressure sensor 1 having a plurality of element rows, as shown in FIG. 2, the area of the substrate 11 is large, and therefore, when the substrate 11 is pressed against the living body, also the range where the radial artery TD is collapsed is widened. Namely, it is seemed that an influence on the blood flow information easily becomes large. Therefore, it is particularly effective to decide the first pressing force by the above-described method.

The invention can be also provided as a program which causes a computer to execute the steps which are to be performed by the controller 3 in the embodiment, and which are shown in FIG. 7. Such a program is recorded on a non-transitory recording medium from which the program can be read by a computer.

For example, such "computer readable medium" includes an optical recording medium such as a CD-ROM (Compact Disc-ROM), a magnetic recording medium such as a memory card, etc. Alternatively, such a program may be provided by download through a network.

The presently disclosed embodiment should be considered in all respects to be illustrative and not restrictive. The scope of the invention is indicated by the appended claims rather than the foregoing description, and all changes which come within the meaning and range of equivalents thereof are intended to be embraced therein.

As described above, the following matters are disclosed in the specification.

The disclosed biological information measurement apparatus includes: a pressure sensor which includes a pressure detecting element; a pressing mechanism which is configured to press the pressure sensor against an artery in a living body; a press controller which is configured to control a pressing force to be exerted by the pressing mechanism; a blood flow sensor which is placed adjacent to the pressure sensor, and which is used for measuring blood flow information indicating a flow of blood that flows through the artery; a blood flow information measurer which is configured to measure blood flow information based on an output signal of the blood flow sensor; a pressing force decider which is configured to decide a first pressing force to be exerted by the pressing mechanism based on blood flow information that is measured by the blood flow information measurer during a pressing force control time period when the pressing force is changed in one direction by a control of the press controller, and information of a pressure pulse wave that is detected by the pressure detecting element during the pressing force control time period; and a record controller which, on a recording medium, is configured to record a pressure pulse wave that is detected by the pressure detecting element in a first state where the pressing force to be exerted by the pressing mechanism is controlled to the first pressing force by the pressing controller, and blood flow information that is measured by the blood flow information measurer in the first state.

In the disclosed biological information measurement apparatus, the pressing force decider is configured to determine a second time period which is in an at least partial time period of a first time period when a change rate of the information of the pressure pulse wave detected during the pressing force control time period is equal to or smaller than a threshold, and which is a continuous time period when the blood flow information is within a predetermined range while setting a timing when the pressing force is controlled to be minimum, as a starting point, and is configured to decide one of pressing forces in the second time period, as the first pressing force.

In the disclosed biological information measurement apparatus, the pressing force decider is configured to select a time period which extends from a timing when the pressing force is controlled to be minimum in the first time period, to a timing when a pressure pulse wave having a maximum amplitude is detected in the first time period, as the at least partial time period of the first time period.

In the disclosed biological information measurement apparatus, the pressing force decider is configured to decide a maximum one of the pressing forces in the second time period as the first pressing force.

In the disclosed biological information measurement apparatus, the pressing force decider is configured to decide the predetermined range based on an average value and standard deviation of the blood flow information measured in a third time period when the pressing force is smaller than the pressing force in the first time period in the pressing force control time period.

In the disclosed biological information measurement apparatus, the pressing force control time period is a time period when the pressing force is changed in an increasing direction by a control of the press controller.

In the disclosed biological information measurement apparatus, the blood flow sensor is placed upstream of the pressure sensor in a blood flow direction in the artery.

In the disclosed biological information measurement apparatus, the blood flow information is a blood flow velocity or a blood flow volume.

In the disclosed biological information measurement apparatus, the pressure sensor has a plurality of element rows each configured by a plurality of pressure detecting elements which are arranged in one direction, and the plurality of element rows are arranged in a direction perpendicular to the one direction.

The disclosed biological information measurement method includes: a press controlling step of controlling a pressing force to be exerted by a pressing mechanism which is configured to press a pressure sensor against an artery in a living body, the pressure sensor including a pressure detecting element for detecting a pressure pulse wave; a blood flow information measuring step of measuring blood flow information based on an output signal of a blood flow sensor which is placed adjacent to the pressure sensor, and which is used for measuring blood flow information indicating a flow of blood that flows through the artery; a pressing force deciding step of deciding a first pressing force to be exerted by the pressing mechanism based on blood flow information measured in the blood flow information measuring step during a pressing force control time period when the pressing force is changed in one direction in the press controlling step, and information of a pressure pulse wave that is detected by the pressure detecting element during the pressing force control time period; and a record controlling step of, on a recording medium, recording a pressure pulse wave that is detected by the pressure detecting element in a first state where the pressing force to be exerted by the pressing mechanism is controlled to the first pressing force in the press controlling step, and blood flow information that is measured in the blood flow information measuring step in the first state.

The disclosed biological information measurement program causes a computer to execute: a press controlling step of controlling a pressing force to be exerted by a pressing mechanism which is configured to press a pressure sensor against an artery in a living body, the pressure sensor including a pressure detecting element for detecting a pressure pulse wave; a blood flow information measuring step of measuring blood flow information based on an output signal of a blood flow sensor which is placed adjacent to the pressure sensor, and which is used for measuring blood flow information indicating a flow of blood that flows through the artery; a pressing force deciding step of deciding a first pressing force to be exerted by the pressing mechanism based on blood flow information measured in the blood flow information measuring step during a pressing force control time period when the pressing force is changed in one direction in the press controlling step, and information of a pressure pulse wave that is detected by the pressure detecting element during the pressing force control time period; and a record controlling step of, on a recording medium, recording a pressure pulse wave that is detected by the pressure detecting element in a first state where the pressing force to be exerted by the pressing mechanism is controlled to the first pressing force in the press controlling step, and blood flow information that is measured in the blood flow information measuring step in the first state.

According to the invention, it is possible to provide a biological information measurement apparatus and biological information measurement method which can accurately detect a pressure pulse wave that is necessary for measuring biological information, while reducing an influence on the measurement accuracy of blood flow information.

Although the invention has been described with reference to the specific embodiment, the invention is not limited to the embodiment, and various changes can be made without departing from the technical spirit of the disclosed invention.

What is claimed is:

1. A biological information measurement apparatus comprising:
a pressure sensor which includes a pressure detector;
a pressing mechanism which is placed adjacent to the pressure sensor and configured to press the pressure sensor against an artery in a living body;
a press controller which is configured to control a pressing force to be exerted by the pressing mechanism;
a blood flow sensor which is placed adjacent to the pressure sensor, and which is used for measuring blood flow information indicating a flow of blood that flows through the artery;
a signal processor which is configured to measure the blood flow information based on an output signal of the blood flow sensor;
a processor which is configured to decide a first pressing force to be exerted by the pressing mechanism based on:
the blood flow information that is measured by the signal processor during a pressing force control time period when the pressing force is either increased or decreased by a control of the press controller; and
information of a pressure pulse wave that is a blood pressure wave, and is detected by the pressure detector during the pressing force control time period; and
a record controller which, on a recording medium, is configured to record the pressure pulse wave that is detected by the pressure detector in a first state where the pressing force to be exerted by the pressing mechanism is controlled to the first pressing force by the press controller, and the blood flow information that is measured by the signal processor in the first state,
wherein the blood flow information is a blood flow velocity,
wherein the processor is configured to:
determine a first time period in which a change rate of the information of the pressure pulse wave detected during the pressing force control time period is equal to or smaller than a threshold;
determine a second time period which is within a part of the first time period and which is a continuous time period in which the blood flow information is within a predetermined range while setting a timing when the pressing force is controlled to be minimum, as a starting point of the second time period;
decide one of pressing forces in the second time period, in which the blood flow velocity is within the predetermined range, to prevent variation of the blood flow velocity being increased, as the first pressing force; and
select a time period which extends from the starting point of the second time period, to a timing when the pressure pulse wave having a maximum amplitude is detected in the first time period, as the part of the first time period,
wherein the blood flow sensor is configured to non-invasively measure the blood flow velocity by an ultrasonic Doppler method or laser Doppler method, and
wherein the pressure detector is configured with a plurality of rows of elements, which are arranged in a horizontal direction perpendicular to a blood flow direction in the artery.

2. The biological information measurement apparatus according to claim 1, wherein
the processor is configured to decide a maximum pressing force of the pressing forces in the second time period as the first pressing force.

3. The biological information measurement apparatus according to claim 1, wherein
the processor is configured to set the predetermined range within one standard deviation of an average value, wherein the average value and the standard deviation are of a set of blood flow velocities measured in a third time period when the pressing force is smaller than the pressing force in the first time period in the pressing force control time period.

4. The biological information measurement apparatus according to claim 1, wherein
the pressing force control time period is a time period when the pressing force is increased by the control of the press controller.

5. The biological information measurement apparatus according to claim 1, wherein
the blood flow sensor is placed upstream of the pressure sensor in a blood flow direction in the artery.

6. A biological information measurement method comprising:
controlling a pressing force to be exerted by a pressing mechanism which is placed adjacent to a pressure sensor and configured to press the pressure sensor against an artery in a living body, the pressure sensor including a pressure detector for detecting a pressure pulse wave that is a blood pressure wave;
measuring blood flow information based on an output signal of a blood flow sensor which is placed adjacent to the pressure sensor, the blood flow sensor used for measuring the blood flow information indicating a flow of blood that flows through the artery;
deciding a first pressing force to be exerted by the pressing mechanism based on:
the blood flow information measured during a pressing force control time period when the pressing force either increased or decreased; and
information of the pressure pulse wave that is detected by the pressure detector during the pressing force control time period; and
on a recording medium, recording the pressure pulse wave that is detected by the pressure detector in a first state where the pressing force to be exerted by the pressing mechanism is controlled to the first pressing force, and the blood flow information that is measured in the first state,
wherein the blood flow information is a blood flow velocity,
wherein the biological information measurement method further comprising:
determining a first time period in which a change rate of the information of the pressure pulse wave detected during the pressing force control time period is equal to or smaller than a threshold;
determining a second time period which is within a part of the first time period and which is a continuous time period in which the blood flow information is within a predetermined range while setting a timing when the pressing force is controlled to be minimum, as a starting point of the second time period, and
selecting a time period which extends from the starting point of the second time period, to a timing when the pressure pulse wave having a maximum amplitude is detected in the first time period, as the part of the first time period, wherein in the deciding, one of pressing forces in the second time period is decided as the first pressing force, in which the blood flow velocity is within the predetermined range, to prevent a variation of the blood flow velocity being increased, wherein the blood flow sensor is configured to non-invasively measure the blood flow velocity by an ultrasonic Doppler method or a laser Doppler method, and wherein the pressure detector is configured with a plurality of rows of elements, which are arranged in a horizontal direction perpendicular to a blood flow direction in the artery.

7. A non-transitory computer readable medium in which a program causing a computer to execute the method according to claim 6 is recorded.

* * * * *